United States Patent [19]
Kihira

[11] Patent Number: 5,691,811
[45] Date of Patent: Nov. 25, 1997

[54] METHOD OF AND APPARATUS FOR DETECTING DEFECT OF TRANSPARENT SHEET AS SHEET GLASS

[75] Inventor: Hiroshi Kihira, Matsusaka, Japan

[73] Assignee: Central Glass Company, Limited, Yamaguchi, Japan

[21] Appl. No.: 598,291

[22] Filed: Feb. 8, 1996

[30] Foreign Application Priority Data

Feb. 10, 1995 [JP] Japan ................................ 7-022432

[51] Int. Cl.⁶ .................................................. G01N 21/00
[52] U.S. Cl. .......................... 356/237; 356/430; 250/562; 250/563
[58] Field of Search ........................ 356/237, 429, 356/430; 250/562, 563

[56] References Cited

U.S. PATENT DOCUMENTS 5,452,079  9/1995  Okugawa .

FOREIGN PATENT DOCUMENTS

0060160   9/1982  European Pat. Off. .
61-176838  8/1986  Japan .
61-176839  8/1986  Japan .
1-189549   7/1989  Japan .
3-027343   3/1991  Japan .

*Primary Examiner*—Frank G. Font
*Assistant Examiner*—Reginald A. Ratliff
*Attorney, Agent, or Firm*—Keck, Mahin & Cate

[57] ABSTRACT

A method of detecting a defect of a transparent sheet is provided in which light source casts light on a transparent sheet through a slit plate, a camera receives the light transmitted through the transparent sheet and produces an image for inspection of a defect, an image of the slit plate produced by the camera is out of focus and represented by a waveform which is representative of brightness of the light transmitting portions and shading portions of the slit plate, and the camera is set to focus on a point where the difference between a maximum brightness and a minimum brightness represented by the waveform becomes minimum or on a point adjacent thereto. An apparatus for detecting a defect of a transparent sheet is also provided.

8 Claims, 6 Drawing Sheets

METHOD OF AND APPARATUS FOR DETECTING DEFECT OF TRANSPARENT SHEET AS SHEET GLASS

BACKGROUND OF THE INVENTION

1. Field of the Invention

The present invention relates to a method of and apparatus for detecting, among various defects, a defect that is caused by distortion such as "knots", "cords" or "striae", unmelted particles or "stones", "bubbles", etc.

2. Description of Related Arts

A known method utilizes a one-dimensional camera for detecting a shadow caused by interception of light by an internal or surface defect of a transparent sheet as disclosed in Japanese Patent Provisional Publication No. 1-189549. Another known method utilizes a point light source for casting a light through a transparent sheet on a screen and a sensor for detecting a defect in a projected figure as disclosed in Japanese Patent Provisional Publication No. 3-27343. A further known method is adapted to observe a row of parallel lines through a transparent sheet so that due to a difference in refraction a defect is represented by distortion of the lines as disclosed in Japanese patent provisional publication Nos. 61-176838 and 61-176839. A further known method utilizes transmission and reflection of a laser beam for detection of a transparent sheet.

A problem of the prior art methods is that detection of a defect caused by distortion such as "knots", "cords", etc. cannot be attained with assuredness and at low cost.

SUMMARY OF THE INVENTION

According to an aspect of the present invention, there is provided a method of detecting a defect of a transparent sheet wherein a light source casts light on the transparent sheet through a screen having a row of light transmitting portions and shading portions and a camera receives the light transmitted through the transparent sheet and produces an image for inspection of the defect, wherein an image of the screen produced by the camera is out of focus and represented by a waveform which is representative of brightness of the light transmitting portions and the shading portions of the screen and wherein the camera is set to focus on a point where the difference between a maximum brightness and a minimum brightness represented by the waveform becomes minimum or on a point adjacent thereto.

According to another aspect of the present invention, there is provided an apparatus for detecting a defect of a transparent sheet, which comprises a light source located on one of opposite sides of the transparent sheet, a screen having a row of alternate light transmitting portions and shading portions and located adjacent to the light source so that light from the light source is cast therethrough on the transparent sheet, and a camera located on the other of the opposite sides of the transparent sheet for receiving the light transmitted through the transparent sheet, wherein an image of the screen produced by the camera is out of focus and represented by a waveform which is representative of brightness of the light transmitting portions and the shading portions of the screen, and wherein the camera is set to focus on a point where the difference between a maximum brightness and a minimum brightness represented by said waveform becomes minimum or on a point adjacent thereto.

The prior art method, for example, disclosed by Japanese patent provisional publication No. 61-176838, is adapted to detect a defect of a transparent sheet by making the defect be represented by disorder or disturbance of alternate light transmitting portions and shading portions of a slit plate in the form of parallel lines which are arranged in row, so the camera is set to focus on the slit plate. By the prior art method, it is impossible to distinguish a small or minute defect caused by distortion and a defect caused by a particle or speck of dust or dirt, so in the case of detecting a defect of a transparent sheet caused by distortion an erroneous detection is likely occur.

According to the present invention, an image of a defect of a transparent sheet is adapted to be picked up by a camera which is set to focus on a point where the difference between a maximum brightness and a minimum brightness of a waveform which is representative of the brightness of light transmitting portions and shading portions of a slit plate, becomes minimum or set to focus on a point adjacent thereto. Specifically, the camera is set to focus on the point which is located neither on the slit plate nor on the transparent sheet. By this, in the case where the transparent sheet does not have any defect, the camera does not produce any clear image but allows its monitor television to have a screen of a gray color resulting from the combination of the black of the shading portions (dark portions) and the white of the light transmitting portions (light portions) of the slit plate, and the brightness represented by the signal waveform is maintained at a constant level intermediate between the maximum brightness and the minimum brightness. When the transparent sheet has a particle or speck of dust or dirt, the dust or dirt is represented by an obscure black spot, so the signal waveform has a low brightness portion only at a place corresponding to the black spot. On the other hand, when the transparent sheet has a defect caused by distortion, the defective portion of the transparent sheet is represented by a clear image of the pattern of the slit plate, i.e., a clear image of a pattern including a light section, dark section and light section or a dark section, light section and dark section which are arranged in this order, so making it possible to distinguish a defect to be detected from a defect caused by a particle of dust or dirt adhered to the transparent sheet.

Further, since the camera is not set to focus on the transparent sheet, it becomes possible to reduce an influence resulting from a particle of dust or dirt adhered to the transparent sheet or other disturbance in detection.

The above structure is effective for overcoming the above noted problem inherent in the prior art device.

It is accordingly an object of the present invention to provide a novel and improved method of detecting a defect of a transparent sheet which can detect a defect caused by distortion, particularly a small or minute defect, with assuredness and at low cost.

It is a further object of the present invention to provide a method of the foregoing character which is suited for automatic detection.

It is a further object of the present invention to provide a method of the foregoing character which can distinguish a defect caused by distortion from a defect caused by a particle of dust or dirt adhered to the transparent sheet, with assuredness and at low cost.

It is a further object of the present invention to provide a novel and improved apparatus for carrying out the method of the foregoing character.

DETAILED DESCRIPTION OF THE EMBODIMENTS

Figure 1:
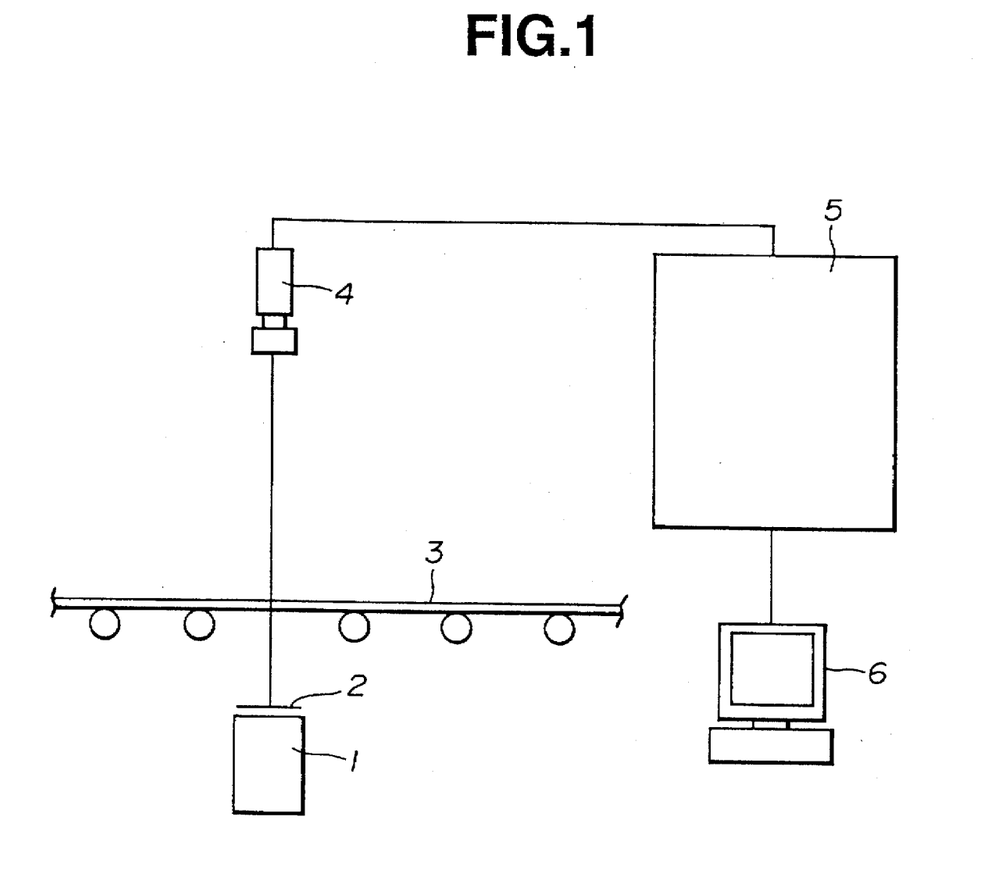
FIG. 1 is a schematic view of an apparatus for carrying out a method of detecting a defect of a transparent sheet according to an embodiment of the present invention.
Figure 2:
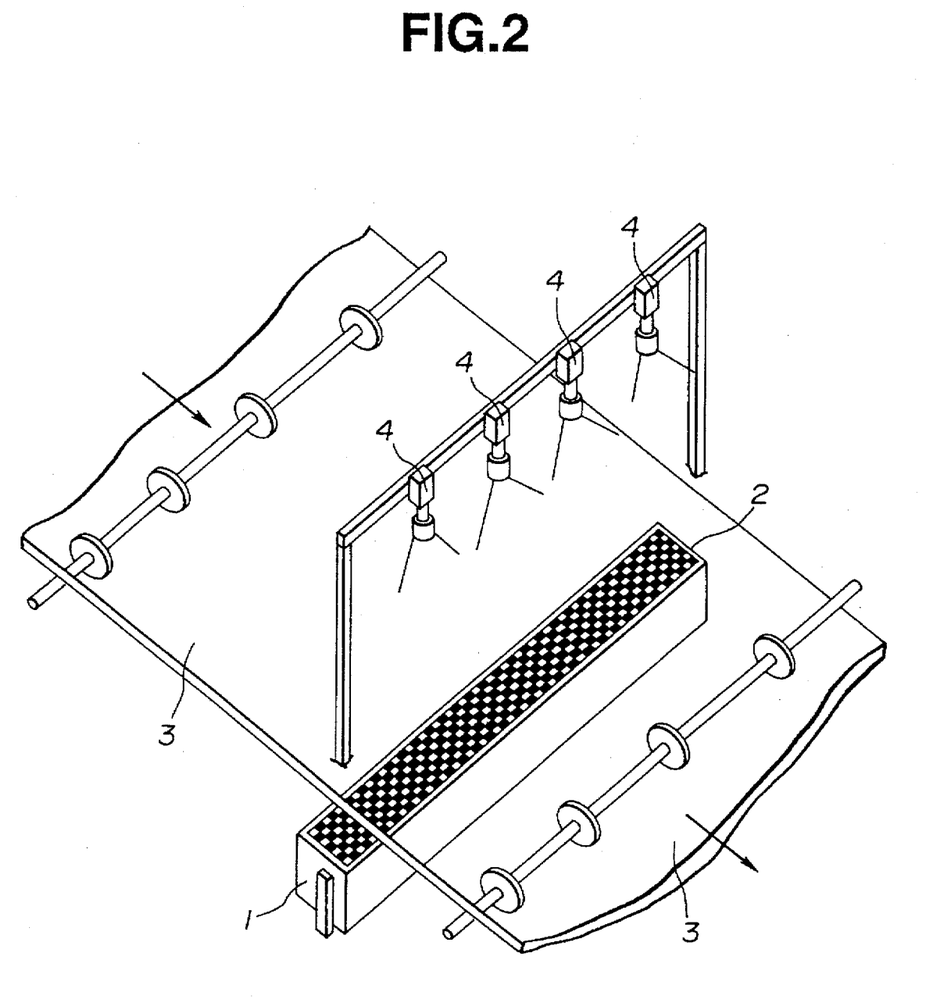
FIG. 2 is a perspective view of a principal portion of the apparatus of FIG. 1, the apparatus being provided with a slit plate having light transmitting portions and shading portions which are arranged in a checkered pattern.

Referring first to FIGS. 1 and 2, a light source 1 consists of a box having an upper open end, a light source, e.g., a fluorescent light installed in the box and a transparent plate attached to the upper open end of the box. A screen or slit plate 2 has a plurality of alternate small light transmitting portions and shading portions which are arranged in a checkered pattern. The light transmitting portions are 1 mm wide and the shading portions are 1 mm wide, respectively. The slit plate 2 is formed from a transparent sheet or plate and has the light transmitting portions and the shading portions which are arranged alternately in line. In use, the slit plate 2 is placed on the above described transparent sheet and adhered or otherwise secured thereto, and is sized so as to be larger in width than a transparent sheet 3 for inspection. Any light source other than the above described one can be used, provided that it is a popular light source for one-dimensional camera.

A plurality of one-dimensional cameras 4 using CCD (charge coupled device) are arranged on the side of the transparent sheet 3 opposite to the light source 1, i.e., arranged in line extending across the transparent sheet 3 and in such a manner that the transparent sheet 3 is interposed between the cameras 4 and the light source 1. Each camera 4 is set perpendicularly to the upper surface of the transparent sheet 3 and in such a manner that its scanning line crosses at right angles the direction in which the transparent sheet 3 is conveyed or runs and that the light having transmitted through the light transmitting portions of the slit plate 2 can be within the field of view of the camera 4. In actual use, the plurality of cameras 4 are arranged in the above described manner in order to obtain a field of view covering the width of the transparent sheet 3. The signals produced by the one-dimensional cameras 4, which are representative of the brightness of the image picked up by the cameras 4, are inputted to an image processing unit 5 to be processed thereby for detection of a defect of a transparent sheet.

The operation of the apparatus of this invention will be described hereinbelow.

Figure 3A:
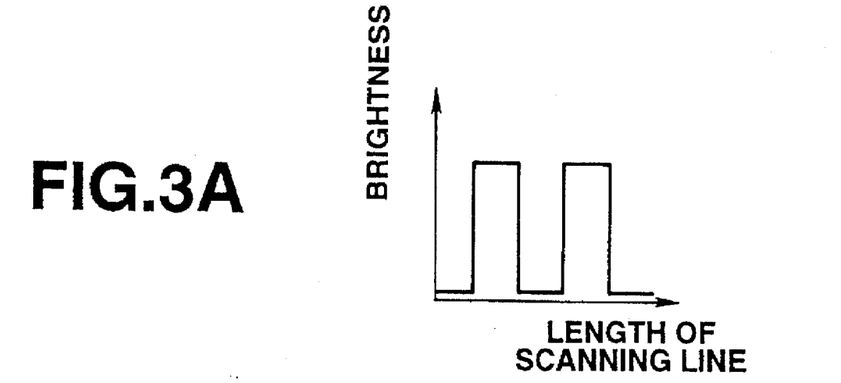
FIG. 3A shows a waveform representative of the brightness of an image of the slit plate of FIG. 1 when a camera is set to focus on the slit plate, wherein a light image portion represents a light transmitting portion and a dark image portion represents a shading portion of the slit plate.
Figure 3B:
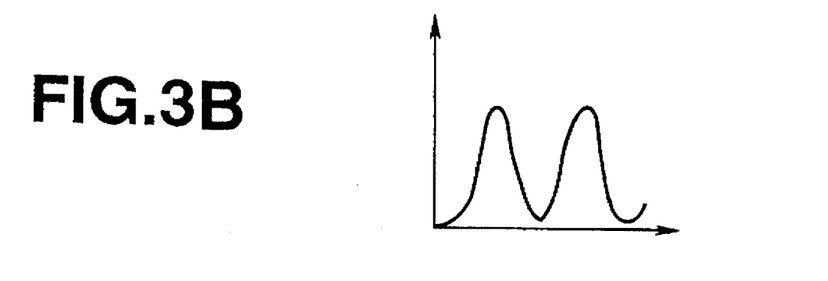
FIG. 3B shows a waveform similar to that of FIG. 3A but obtained when the focus of the camera is displaced a little from the slit plate.
Figure 3C:
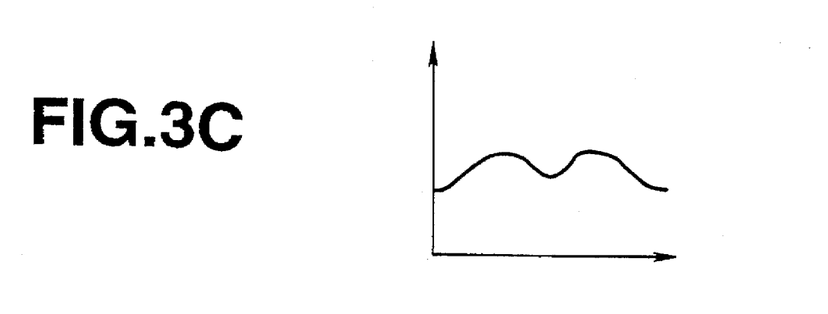
FIG. 3C shows a waveform similar to that of FIG. 3B but obtained when the focus of the camera is displaced further from the slit plate.
Figure 3D:
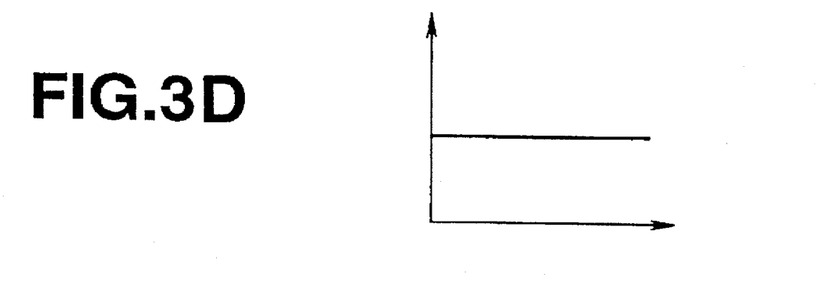
FIG. 3D shows a waveform similar to that of FIG. 3C but obtained when the focus of the camera is displaced yet further from the slit plate so as to make the difference between a maximum brightness and a minimum brightness represented by the waveform become minimum and flat.

In the first step, each one-dimensional camera 4 is set to focus on the slit plate 2 and picks up an image of the slit plate 2. When this is the case, signals inputted to each camera 4 to represent the brightness of the light transmitting portions and shading portions of the slit plate 2 take the form of a square waveform as shown in FIG. 3A, in which the light transmitting portions are represented by light image portions (white portions) having a higher brightness and the shading portions are represented by dark image portions (black portions) having a lower brightness. When the focus of each camera 4 is displaced gradually from the slit plate 2, the waveform representative of the brightness of the light transmitting portions and shading portions of the slit plate 2 is caused to decay as shown in FIG. 3B, so that the borderline between the light image portion and the dark image portion is becoming unclear. When the focus of each camera 4 is displaced further from the slit plate 2, the waveform representative of the brightness of the light transmitting portions and shading portions of the slit plate 2 decays further as shown in FIG. 3C, causing the peak and bottom of the waveform, i.e., the light image portion and the dark image portion to overlap and come closer to each other, and finally causing the waveform to become flat at or nearly at a brightness level intermediate between the light image portion (maximum brightness) and the dark image portion (minimum brightness), as shown in FIG. 3D. Upon detection of a defect of a transparent sheet, the focal distance of each camera 4 is set or adjusted so as to attain the condition shown in FIG. 3D, i.e., each camera 4 is set to focus on a point where the difference between the maximum brightness and the minimum brightness represented by the waveform becomes minimum or on a point adjacent thereto.

Figure 4A:
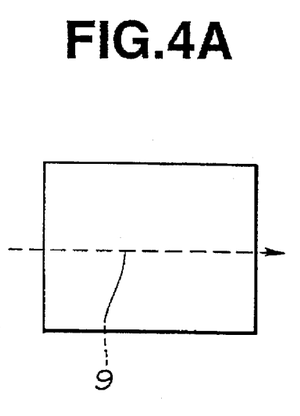
FIG. 4A shows an image of a transparent sheet produced by the camera of the apparatus of FIG. 1 when the focus of the camera is adjusted to attain the condition of FIG. 3D and when the transparent sheet for inspection does not have any defect caused by distortion and any particle of dust or dirt.
Figure 4B:
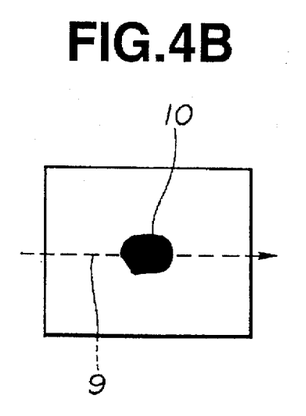
FIG. 4B shows an image produced in the similar manner to that of FIG. 4A but obtained when the transparent sheet has a particle of dust or dirt.
Figure 5A:
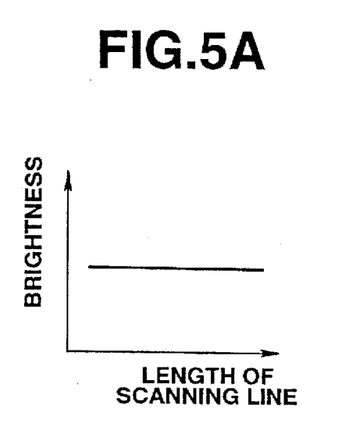
FIG. 5A shows a waveform obtained in the similar manner to that of FIG. 3D but when the transparent sheet does not have any defect caused by distortion and any particle of dust or dirt as represented by the image of FIG. 4A.

An image of the transparent sheet 3 is picked up under the condition described as above, i.e., under the focal condition shown in FIG. 3D. When an image of a transparent sheet 3 which does not have any defect caused by distortion and any dust or dirt is picked up by the camera 4, such an image shown in FIG. 4A is produced by the monitor television of the camera 4. In this connection, the waveform representative of the brightness of a portion of the transparent sheet 3 located on the scanning line 9 takes such a shape shown in the FIG. 5A, in which the brightness is taken as ordinate and the length of the scanning line is taken as abscissa, i.e., a flat shape at or nearly at a brightness level intermediate between the light image portion (maximum brightness) and the dark portion (minimum brightness) of the image of the slit plate 2.

Figure 5B:
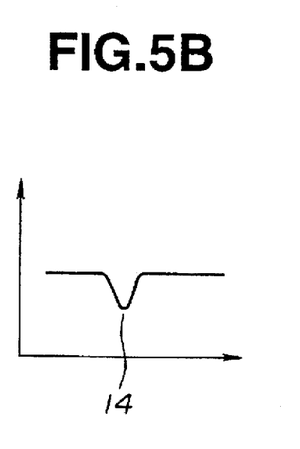
FIG. 5B shows a waveform obtained in the similar manner to that of FIG. 5A but when the transparent sheet has a particle of dust or dirt as represented by the image of FIG. 4B.

When the transparent sheet 3 has a particle of dust or dirt sticking thereto and the image of the portion of the transparent sheet 3 at which the particle of dust or dirt is located is picked up by the camera 4, such an image shown in FIG. 5B is produced by the monitor television of the cameras 4. In this connection, the waveform representative of the brightness of the portion of the transparent sheet 3 located on the scanning line 9 takes such a shape shown in FIG. 5B, i.e., the waveform has a low brightness portion at a location corresponding to the portion of the transparent sheet 3 where the particle of dust or dirt is located.

Figure 4C:
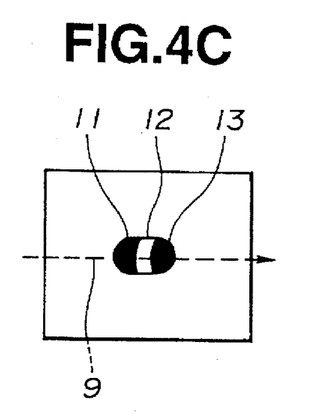
FIG. 4C shows an image produced in the similar manner to that of FIG. 4A but obtained when the transparent sheet has a defect caused by distortion.
Figure 5C:
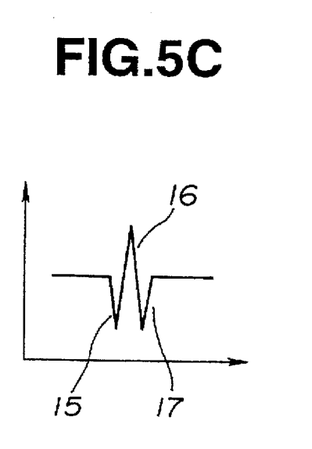
FIG. 5C shows a waveform obtained in the similar manner to that of FIG. 5A but when the transparent sheet has a defect caused by distortion as represented by the image of FIG. 4C.

When the camera 4 picks up the image of a transparent sheet 3 having a small or minute defect caused by distortion, such an image shown in FIG. 4C is produced by the monitor television of camera 4, in which the transparent sheet portion having a small defect caused by distortion is represented by a clear flag-like pattern consisting of a black section 11, white section 12 and a black section 13. In this connection, the waveform representative of the brightness of the portion of the transparent sheet 3 located on the scanning line 9 extending through the flag-like pattern takes such a form shown in FIG. 5C, i.e., such a form consisting of a dark portion 15, light portion 16 and dark portion 17 corresponding to the black section 11, white section 12 and black section 13 of the flag-like pattern, respectively. From this, it will be seen that in the case where the transparent sheet 3 has a defect caused by distortion the image and waveform produced by the camera 4 are largely different from those obtained when a particle of dust or dirt is adhered to the transparent sheet 3. This is because the light transmitting portion in white and the shading portion in black of the slit plate 2 are picked up to produce a clear image due to refraction of lights caused by the distortion at the defective portion of the transparent sheet 3 and due to the above described adjustment of the focal distance of the camera 4.

Figure 7A:
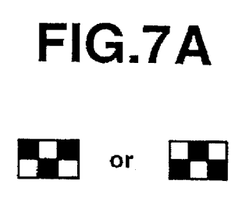
FIGS. 7A to 7C are images produced by the camera of the apparatus of FIG. 1 when the focus of the camera is adjusted to attain the condition of FIG. 3D, a transparent sheet for inspection has a defect caused by distortion and the slit plates of FIGS. 6A to 6C are used, respectively.
Figure 7B:
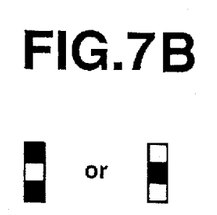
Figure 7C:
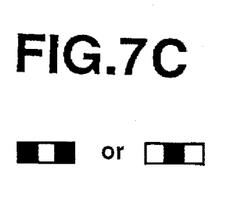
Figure 8:
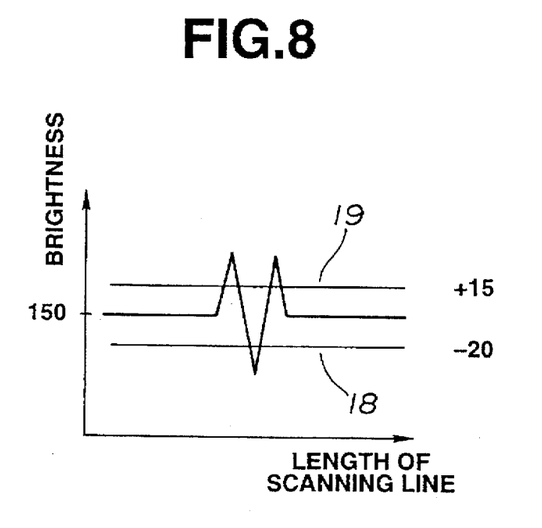
FIG. 8 shows a waveform obtained in the similar manner to that of FIG. 3D but when a transparent sheet for inspection has a defect caused by distortion.

In the camera 4 which is set to focus at a predetermined distance, i.e., which is set to have a predetermined focal length as described above, the brightness (intermediate brightness level) indicated by the waveform when the transparent sheet 3 does not have any particle of dust or dirt or any defect caused by distortion is assumed to be 150 as shown in the graph of FIG. 8. In this connection, when the transparent sheet 3 having a small defective portion caused by distortion is picked up by the camera 4 and such a waveform as shown in FIG. 7 is obtained along a scanning line extending through the defective portion of the transparent sheet 3, a slice level 18 used for determination of a dark portion is set so as to be lower than the intermediate brightness level by 20–30 such that the brightness lower than the slice level 18 is determined as representing a dark image portion, whilst on the other hand a slice level 19 used for determination of a light image portion is set so as to be higher than the intermediate brightness level by 15–20 such that the brightness higher than the slice level 19 is determined as representing a light image portion. In this manner, when the image brightness indicating waveform includes a light image portion, dark image portion and a light image portion which are arranged in this order or a black image portion, light image portion and a black image portion which are arranged in this order, it is determined that the portion of the transparent sheet 3 corresponding to that waveform is defective. The scanning line crossing the defective portion of the transparent sheet 3 is of the width corresponding the width of one picture element by which the resolution of the one-dimensional camera 4 is determined, so a similar waveform is obtained continuously when the defective portion is of the size larger than a predetermined amount since the defective portion is displaced as the transparent sheet 3 is conveyed. In this connection, when a similar waveform is obtained continuously, it is determined that the waveform indicates one defective portion. The above described determinations or judgments are made by a personal computer 6 in response to signals from the image processing unit 5.

The pattern consisting of a light portion, a dark portion and a light portion or a dark portion, a light portion and a dark portion is determined depending upon the pattern of the slit plate 2 upon which the defective portion is located.

Figure 6A:
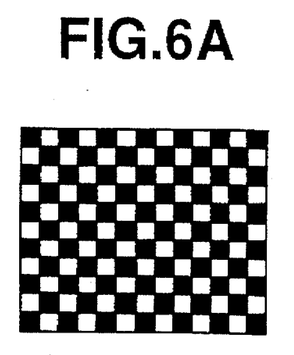
FIGS. 6A to 6C are various patterns for the slit plate of the apparatus of FIG. 1, in which dark portions represent shading portions and light portions represent light transmitting portions of the slit plate.

When the slit plate 2 has such a checkered pattern as shown in FIG. 6A, the defective portion of the transparent sheet 3 caused by distortion is represented by such a pattern shown in FIG. 7A, i.e., a pattern consisting of a light portion, a dark portion and a light portion or a dark portion, a light portion and a dark portion which are arranged in this order in the direction of extension of a scanning line or a combination of those patterns.

Further, the data concerning the kind, size, etc. of the above described defect can be supplied to a personal computer 6 or the like for totalization and used as information for various controls. Further, the defect can be detected at the moment or instance and its position can be found specifically, so a mark is put on a defective portion of a transparent sheet and at a later process the marked portion is found so that the defective portion is automatically cut off and removed.

Referring to FIGS. 6B, 6C, 7B and 7C, further embodiments will be described. The embodiments are substantially similar to the previous embodiment described with reference to FIGS. 1–2, 3A–3D, 4A–4D, 5A–5D, 6A, 7A and 8 except that the slit pate 2 has alternate light transmitting portions and shading portions in the form of a row of parallel lines, which row is arranged in parallel to or so as to cross the direction of conveyance of the transparent sheet 3 at right angles, and which light transmitting portions and shading portions are arranged with equal intervals, for example, each light transmitting portion being 1 mm wide and each shading portion being 1 mm.

Figure 6B:
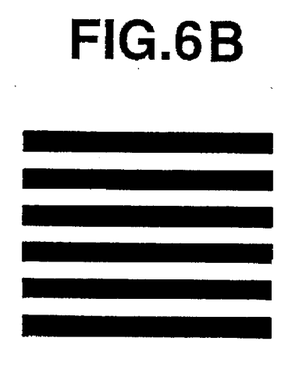

In this instance, in the case where the slit plate 2 has a pattern shown in FIG. 6B, i.e., the row of light transmitting and shading portions of the slit plate 2 is arranged so as to cross the transparent sheet 3 conveying direction at right angles or in other words the scanning direction of the one-dimensional camera 4 and the row of light transmitting and shading portions of the slit plate 2 are parallel to each other, the defective portion of the transparent sheet 3 is represented by such a pattern shown in FIG. 7B, i.e., a pattern consisting of a dark portion, light portion and dark portion or a light portion, dark portion or light portion which are arranged in this order in the transparent sheet conveying direction.

Figure 6C:
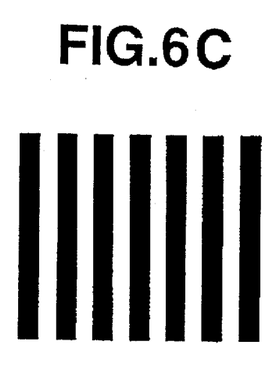

In the case where the slit plate 2 has such a pattern shown in FIG. 6C, i.e., the row of light transmitting portions and shading portions of the slit plate 2 is arranged in parallel with the direction of conveyance of the transparent sheet 3 or in other words the scanning direction of the one-dimensional camera 4 and the row of light transmitting and shading portions of the slit plate 2 are arranged so as to cross each other at right angles, the defective portion of the transparent sheet 3 is represented by such a pattern shown in FIG. 7C, i.e., a pattern consisting of a dark portion, light portion and dark portion or a light portion, dark portion and light portion which are arranged in this order in the direction in which the scanning line is elongated.

Figure 9:
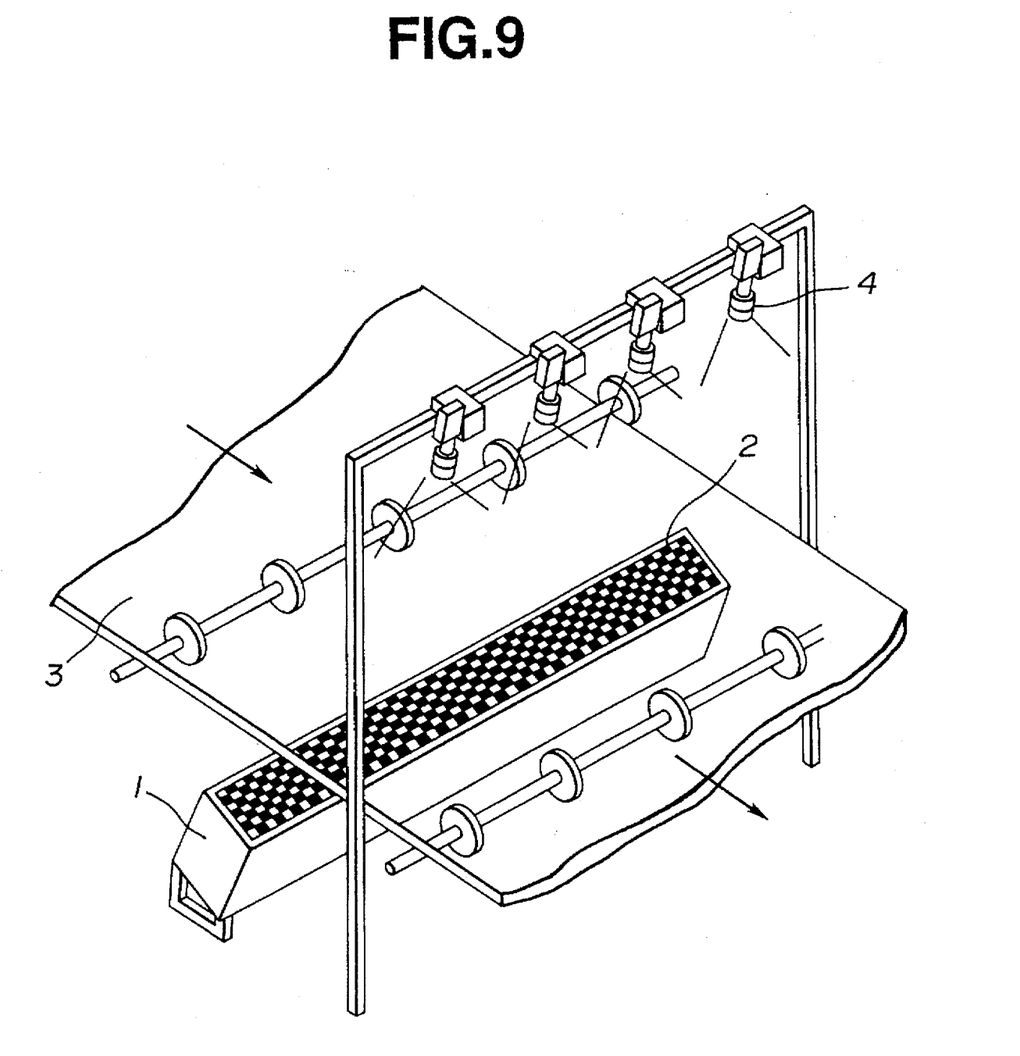
FIG. 9 is a view similar to FIG. 2 but shows a further embodiment of the present invention.

Referring to FIG. 9, a further embodiment will be described. This embodiment is substantially similar to the previous embodiment described with reference to FIGS. 1–2, 3A–3D, 4A–4D, 5A–5D, 6A, 7A and 8 except that the line in which the light source 1, slit plate 2 and one-dimensional camera 4 are arranged is not perpendicular to the surface of the transparent sheet 3 for inspection but inclined with respect to the same. By such an arrangement, it is also possible to detect a fine or small defect of a transparent sheet assuredly similarly to the previous embodiment.

In the foregoing, it is to be noted that the present invention is desirable particularly when used to detect a fine or small defect of the size of about 0.5 mm for instance.

It is further to be noted that the checkered pattern shown in FIG. 6A is desirable for the screen or slit plate 2 since it is useful for analyzation of both the size of a defect and the direction (longitudinal direction or lateral direction) in which a defect is extended.

It is further to be noted that the screen or slit plate 2 having alternate light transmitting portions and shading portions can be produced by applying or printing ink, paint, past or the like on a transparent film made of a resinous material, thin plate glass or the like so as to form a coating for the shading portions.

It is further to be noted that, other than a checkered pattern or a pattern in the form of a row of parallel lines for a screen or slit plate, a pattern like a lattice work, a honeycomb-like pattern having hexagonal openings, a grille-like pattern having rhombus openings, a pattern having dot-like shading portions arranged vertically or horizontally, or the like pattern can be used to produce substantially the same effect.

It is further to be noted that the one-dimensional CCD camera 4 can be of the type using MOS other than CCD for use as an image pick-up device.

It is further to be noted that the present invention can be used for detecting a defect of a transparent sheet made of a resinous material other than a sheet glass.

What is claimed is:

1. A method of detecting a defect of a transparent sheet wherein a light source casts light on the transparent sheet through a screen having a row of alternate light transmitting portions and shading portions and a one-dimensional camera receives the light transmitted through the transparent sheet and produces an image for inspection of the defect comprising the steps of:

representing an image of said screen produced by said camera which is out of focus by a waveform which is representative of brightness of said light transmitting portions and said shading portions of said screen, setting said camera to focus on a point where the difference between a maximum brightness and a minimum brightness represented by said waveform becomes minimum or on a point adjacent thereto, said image produced by said camera including light image portions and dark image portions corresponding to said light transmitting portions and shading portions of said screen, said waveform being representative of brightness of said light image portions and dark image portions which are located on one scanning line.

arranging said light transmitting portion and said shading portions of said screen in a checkered pattern, and determining that a portion of the transparent sheet corresponding to said waveform is defective when said waveform includes a light image portion, a dark image portion and a light image portion arranged in order or a dark image portion, a light image portion and a dark image portion arranged in order.

2. A method according to claim 1, and further comprising the step of setting said camera perpendicularly to a surface of the transparent sheet.

3. A method according to claim 1, and further comprising the step of setting said camera so as to form an angle with respect to a line normal to a surface of the transparent sheet.

4. A method according to claim 1, and further comprising the step of arranging a plurality of said cameras in a line extending across the direction of conveyance of the transparent sheet.

5. An apparatus for detecting a defect of a transparent sheet, comprising:

a light source located on one of opposite sides of the transparent sheet;

a screen having a row of alternate light transmitting portions and shading portions and located adjacent said light source so that light from said light source is cast therethrough on the transparent sheet; and a one-dimensional camera located on the other of the opposite sides of the transparent sheet for receiving the light transmitted through the transparent sheet;

wherein an image of said screen produced by said camera is out of focus and represented by a waveform which is representative of brightness of said light transmitting portions and said shading portions of said screen, said camera is set to focus on a point where the difference between a maximum brightness and a minimum brightness represented by said waveform becomes minimum or on a point adjacent thereto, said image produced by said camera includes light image portions and dark image portions corresponding to said light transmitting portions and shading portions of said screen, said waveform is representative of brightness of said light image portions and dark image portions which are located on one scanning line, and said light transmitting portions and said shading portions of said screen are arranged in a checkered pattern so that when said waveform includes a light image portion, a dark image portion and a light image portion arranged in order or a dark image portion, a light image portion and a dark image portion arranged in order, it is determined that a portion of the transparent sheet corresponding to said waveform is defective.

6. An apparatus according to claim 5, wherein said camera is set to receive a ray of light which is perpendicular to a surface of the transparent sheet.

7. An apparatus according to claim 5, wherein said camera is set to receive a ray of light which inclines with respect to a line normal to a surface of the transparent sheet.

8. A method according to claim 5, wherein a plurality of said cameras is arranged in a line extending across the direction of conveyance of the transparent sheet.

\* \* \* \* \*